United States Patent
Lee et al.

(10) Patent No.: US 6,590,139 B1
(45) Date of Patent: Jul. 8, 2003

(54) METHOD FOR PRODUCING CLONED COWS

(75) Inventors: Byeong-Chun Lee, Seoul (KR); Tae-Young Shin, Seoul (KR); Sang-Ho Roh, Kyunggi-do (KR); Jeong-Muk Lim, Seoul (KR); Jong-Im Park, Seoul (KR); Jong-Ki Cho, Seoul (KR); Ki-Yon Kim, Seoul (KR); Eun-Song Lee, Kangwon-do (KR); Soo-Jung Shin, Seoul (KR); Sung-Ki Kim, Kyunggi-do (KR); Kil-Young Song, Seoul (KR); Woo-Suk Hwang, 11-2 Nonhyun-dong, Kangnam-gu, Seoul (KR), 135-010

(73) Assignee: Woo-Suk Hwang, Seoul (KR)

( * ) Notice: Subject to any disclaimer, the term of this patent is extended or adjusted under 35 U.S.C. 154(b) by 0 days.

(21) Appl. No.: 09/701,839

(22) PCT Filed: Jun. 30, 2000

(86) PCT No.: PCT/KR00/00707

§ 371 (c)(1),
(2), (4) Date: Dec. 4, 2000

(87) PCT Pub. No.: WO01/00795

PCT Pub. Date: Jan. 4, 2001

(30) Foreign Application Priority Data

Jun. 30, 1999 (KR) ............................................. 99-26163
Jun. 30, 1999 (KR) ............................................. 99-26164
Jun. 30, 1999 (KR) ............................................. 99-26165
Jun. 30, 1999 (KR) ............................................. 99-26166

(51) Int. Cl.$^7$ ...................... C12N 15/00; A01K 67/00; A01K 67/33; A01K 67/027
(52) U.S. Cl. ............................... 800/24; 800/8; 800/14; 800/15
(58) Field of Search ............................... 800/3, 18, 21, 800/22, 25, 24, 8, 14, 15

(56) References Cited

U.S. PATENT DOCUMENTS

| | | | |
|---|---|---|---|
| 5,496,720 A | * | 3/1996 | Susko-Parrish et al. .. 435/240.2 |
| 5,945,577 A | | 8/1999 | Stice et al. .................... 800/24 |
| 6,011,197 A | | 1/2000 | Strelchenko et al. .......... 800/24 |

FOREIGN PATENT DOCUMENTS

| | | |
|---|---|---|
| WO | WO 97/07668 | 3/1997 |
| WO | WO 97/07669 | 3/1997 |

OTHER PUBLICATIONS

Sun et.al.; Sex related differences in the calpain system in skeletal muscle of Korean native cattle, 1997, J. Anim. Sci. 75: 173.*
Campbell et.al.; The Science of Providing Milk for Man, 1975, Breeds of Dairy Cattle: 51–58.*
K.H.S. Campbell et al., Nature, 380:64–66 (Mar. 1996).
I. Wilmut et al.,Nature, 385:810–813 (Feb. 1997).
T. Wakayama et al., Nature, 394:369–374 (1998).
R. Prochazka et al., J. Reprod. Fert., 96:725–734 (1992).
C. Kubota et al., Proc. Natl. Acad. Sci., USA, 97:990–995 (2000).
V. Zakhartchenko et al., J. Reproduction and Fertility, 115:325–331, (1999).
J.R. Hill et al., Biology of Reproduction, 62:1135–1140, (2000).
D.N. Wells et al., Reprod. Fertil. Dev., 10:615–626, (1998).
T. Wakayama et al., Nature, 394: 369–374 (1998).
S.L. Stice et al., Theriogenology, 49:129–138, (1998).
A.W.S. Chan et al., Proc. Natl. Acad. Sci, USA, 95:14028–14033, (1998).
G.E. Corley–Smith et al., Molecular Reproduction and Development, 53:363–367, (1999).
K.H.S. Campbell, Seminars in Cell & Developmental Biology, 10:245–252, (1999).
K. Takeda et al., J. Reproduction and Fertility, 116:253–259, (1999).
A.T. Byrne et al., J. Reproduction and Fertility, 117:97–105, (1999).
V. Zakhartchenko et al., Molecular Reproduction and Development, 54:264–272, (1999).
R.P. Lanza et al., Science, 288:665–669, (2000).
T. Wakayama et al., Proc. Natl. Acad. Science, USA 96:14984–14989, (1999).
M. Sims et al., Proc. Natl. Acad. Science, USA, 90:6143–6147, (1993).
A.J. Watson et al., Biology of Reproduction, 62:355–364 (2000).
G.E. Corley–Smith et al., Molecular Reproduction and Development, 53:363–367 (1999).
I. Wilmut et al., Reproduction and Fertility Development, 10:639–643, (1998).
Y. Kato et al., Science, 282:2095–2098, (1998).
D.N. Wells et al., Biology of Reproduction, 60:996–1005, (1999).
A.E. Schnieke et al., Science, 278:2130–2133, (1997).
J.B. Cibelli et al., Science, 280:1256–1258, (1998).
S. Iwasaki et al., Biology of Reproduction, 62:470–475, (2000).
Dinnyes et.al.; Somatic Cell Nuclear Transfer: Recent Progress and Challenges, 2002, Cloning and Stem Cells, vol. 4: 81–90.*

* cited by examiner

*Primary Examiner*—Deborah Crouch
*Assistant Examiner*—Thai-An N. Ton
(74) *Attorney, Agent, or Firm*—Darby & Darby

(57) ABSTRACT

The present invention provides a method for producing cloned cows by employing in vitro maturation of oocytes and nuclear transfer techniques. The method comprises collecting donor somatic cell lines from cows; maturing oocytes extracted from an ovary in vitro; enucleating the oocyte by cutting a portion of the zona pellucida and squeezing out a portion of the cytoplasm, including the first polar body; inserting the donor somatic cell into the oocyte; electrofusing the cells to produce embryos; post-activating the embryos; transferring them into surrogate cows to produce cloned calves.

8 Claims, 2 Drawing Sheets

METHOD FOR PRODUCING CLONED COWS

BACKGROUND OF THE INVENTION

Field of the Invention

The present invention relates to a method for producing cloned cows, more specifically, a method for producing somatic cell-derived cloned cows by employing in vitro maturation and subsequent enucleation of oocytes, nuclear transfer, electrofusion and activation of embryos, postactivation and in vitro culture of the embryos and transfer of the embryos into surrogate cows. It also relates to the embryos and cloned cows produced by the method described above.

Background of the Invention

Animals have long been considered to be produced by fertilization involving male and female gametes. However, tremendous efforts have been made on generating cloned animals with the identical appearance and genetic characteristics.

Cloning of zygotes has been known to be possible only in amphibians for 30 years until the success in producing a cloned offspring by substituting a pronucleus of one-cell zygote in mice(see: McGrath and Solter, Science, 220:1300–1302, 1983). Despite this first success in cloning animals, the same success in industrial animals(see: Wakayama et al., Nature, 394:369–374, 1998) has been reported much later since production of cloned mice employing mature oocytes and zygote blastomeres after 2-cell stage have several problems such as decrease in reprogramming.

With regard to the production of cloned industrial animals by nuclear transfer, it was the first report that an offspring was produced in sheep by employing blastomeres of 8- to 16-cell zygote as donor cells(see: Wiladsen, Nature, 320:63–65, 1986). Since then, only the blastomeres of zygote with totipotency by which a cell can be differentiated into every single cell have been considered to be cloned by nuclear transfer. However, through the continuous research effort, the first cloned sheep was produced by introducing nuclei from somatic cells(see: Wilmut et al., Nature, 385:810–813, 1997), thus making correction in the prior developmental theory and enabling many successful examples to be reported in production of cloned cows(see: Wells et al, Reprod. Fertil. and Develop., 10:369–378, 1998) and pigs.

The prior art methods are, however, proven to be less satisfactory in the sense that the yield of embryos produced by nuclear transfer is relatively low, which resulted in the low production rate of cloned animals.

Under the circumstances, there are strong reasons for exploring and developing an improved method for producing the somatic cell-derived embryos in terms of the yield of embryos produced by nuclear transfer.

SUMMARY OF THE INVENTION

In accordance with the present invention, it has been discovered that: the yield of embryos produced by nuclear transfer can be dramatically increased by shortening time of oocyte manipulation and improving the nuclear transfer and activation rate when donor cells are transferred into enucleated oocytes, by which somatic cell-derived cloned cows can be produced in an efficient manner.

A primary object of the present invention is, therefore, to provide a method for producing cloned cows by nuclear transfer of somatic cells.

The other object of the invention is to provide cloned cow embryos produced by the said method.

Another object is to provide somatic cell-derived cloned cows produced by the said method.

BRIEF DESCRIPTION OF THE DRAWINGS

The above and the other objects and features of the present invention will become apparent from the following description given in the conjunction with the accompanying drawings, in which.

DETAILED DESCRIPTION OF THE INVENTION

Figure 1:
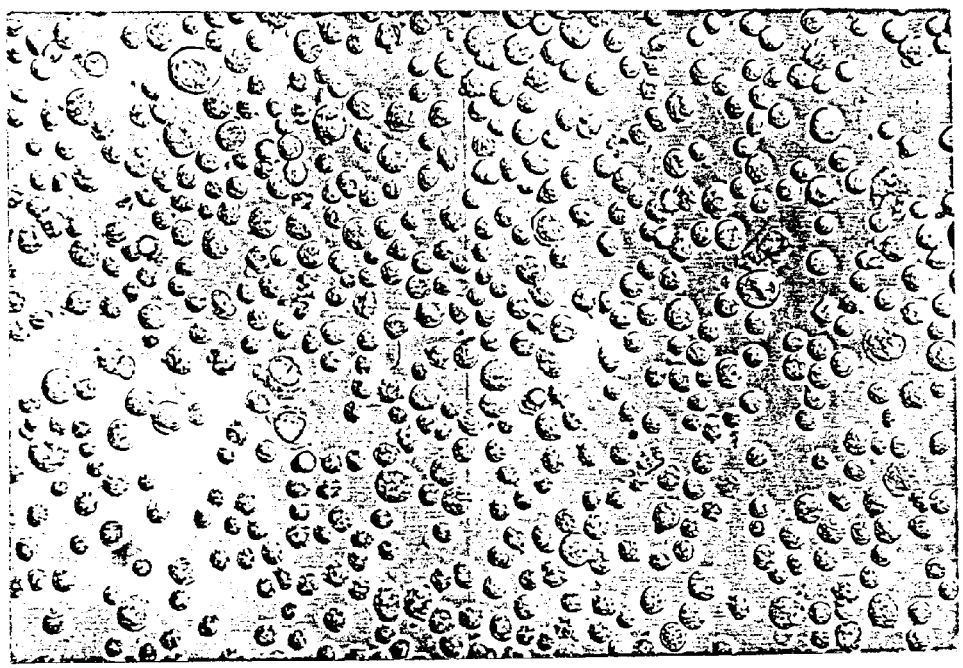
FIG. 1 is a photograph of donor somatic cells.

The method for producing cloned cows of present invention comprises the steps of: preparing donor somatic cell lines collected from cow; maturing oocytes collected from ovary in vitro; removing cumulus cells surrounding the oocytes, cutting a portion of zona pellucida of the matured oocytes and squeezing out a portion of cytoplasm including the first polar body to give enucleated recipient oocytes; transferring a nucleus to the recipient oocyte by injection of the donor cells to the enucleated oocytes, followed by the subsequent electrofusion and activation of the electrofused cells to give embryos; postactivating and culturing the embryos in vitro; and, transferring the cultured embryos into surrogate cows to produce cloned calves.

The method for producing cloned cows of the invention is further illustrated as follows.

Step 1: Preparation of Donor Cells

Somatic cell lines collected from cows are prepared as donor cells: although cow species are not limited for donor cells, Korean cows(*Bos taurus coreane*) and Holstein (*Bos taurus*) are preferred for donor cells. The cell lines obtained from cows include cells collected from uterine flushing fluid, endometrium, oviduct, ear or muscle, cumulus cells or fetal fibroblasts, which are prepared by employing the conventionally known method(see: Mather & Barnes, Methods in Cell Biology, Vol.57, Animal Cell Culture Methods, Academic Press, 1998) with some modifications.

For example, cells are collected by the addition of PBS (phosphate buffered saline) containing 1% penicillin-streptomycin(Gibco; 1000 U/ml penicillin, 10 mg/ml streptomycin) to uterine flushing fluid and subsequent centrifugation. The cells collected from uterine flushing fluid are cultured in DMEM(Dulbecco's modified Eagle's medium) supplemented with non-essential amino acids, 10% FBS(fetal bovine serum) and 1% penicillin-streptomycin under an environment of 39° C., 5% $CO_2$.

Uterine epithelial cells collected from endometrium or oviduct are washed with the said PBS, trypsinized, and cultured under the same conditions as described above.

For cumulus cells, cumulus-oocyte complexes are treated with hyaluronidase solution to isolate cumulus cells surrounding oocytes. The cumulus cells are trypsinized for 30 to 60 minutes under an environment of 39° C., 5% $CO_2$ before they are cultured in a similar manner as described above.

For ear fibroblasts and fetal fibroblasts, they are obtained from the inner side of skin lined along with cartilage tissue and from tissue collected from trunk and limbs of fetus, respectively, by washing and mincing the tissues aseptically, followed by treatment of trypsin and collagenase type II under an environment of 39° C., 5% $CO_2$. These cells are also cultured analogously as in the somatic donor cell lines described above.

The somatic cell lines are stored by subculture, serum starvation culture or freezing. The subculture of donor cell lines is carried out at regular intervals by changing the old medium to new one after trypsinization. The serum starvation culture is performed by employing DMEM supplemented with 0.5% FBS and the method of Wilmut et al. (see: Wilmut et al., Nature, 385:810–813, 1997). The cell lines thus stored are used for later step as donor cells.

Step 2: Preparation of Recipient Oocytes

Immature oocytes collected from ovary are matured in vitro: immature oocytes are selected from ovary in TCM199 washing medium containing 10 mM HEPES(N-[hydroxyethyl]piperazine-N'-[2-ethanesulfonic acid]), and matured by culturing the cells in TCM199 culture medium (containing Na-pyruvate, penicillin-streptomycin) supplemented with estradiol, FSH(follicle stimulating hormone) and FBS for 16 to 22 hr under an environment of 39° C., 5% $CO_2$.

Step 3: Enucleation of Recipient Oocytes

After removing cumulus cells surrounding the mature recipient oocytes and cutting a portion of zona pellucida of the oocytes, a portion of cytoplasm including the first polar body is removed from the oocytes to give enucleated oocytes: first, cumulus cells surrounding the mature oocytes are removed physically with a denuding pipette in TCM199 washing medium containing hyaluronidase. Then, denuded oocytes are washed with TCM199 washing medium and transferred into cytochalasin B solution. For enucleation of the denuded oocytes, a portion of zona pellucida of the denuded oocytes is penetrated by a cutting pipette to give a slit through which 10 to 15% of cytoplasm including the first polar body can be squeezed out of the oocytes. The enucleated oocytes are washed and incubated in TCM199 culture medium. The said cytochalasin B solution is prepared by diluting cytochalasin B dissolved in DMSO (dimethylsulfoxide) with the TCM199 culture medium.

Step 4: Electrofusion of Donor Cells with Recipient Oocytes and Activation of the Electrofused Cells The donor cells are transferred to the recipient oocytes, followed by subsequent electrofusion and activation of the electrofused cells: before the injection of donor cells into recipient oocytes, the enucleated oocytes are washed with TCM199 culture medium and transferred to PHA-P (phytohemagglutinin) solution. Then, the donor cells are transferred to the enucleated oocytes by injecting donor cells to the slit made on zona pellucida of the cocytes in PHA-P solution.

The electrofusion is carried out by employing Electro Cell Manipulator(BTX ECM2001). The reconstructed embryos in mannitol solution supplemented with TCM199 washing solution are placed in a chamber with two electrodes, one on either side. Before placing the embryos with their donor cells facing the cathode in the chamber, the chamber was filled with mannitol solution. After the embryos are electrofused by applying DC pulse of 0.75 to 2.00 kV/cm twice with one second's interval for 15 $\mu s$ each time, the electrofused embryos are washed with mannitol solution and TCM199 washing medium, incubated in cytochalasin B solution, and activated. The electrofusion and activation occur in a simultaneous manner provided that the electrofusion is carried out in a mannitol medium containing $Ca^{2+}$. Otherwise, the activation is performed after electrofusion. When the electrofusion is carried out in a $Ca_{2+}$-free mannitol medium, the activation step is performed by incubating the embryos in ionomycin solution in the dark. Then, ionomycin is removed from the embryos by washing them with TCM199 washing medium containing FBS or BSA. The said ionomycin solution is prepared by diluting ionomycin dissolved in DMSO with TCM199 washing medium containing BSA.

Step 5: Postactivation and in vitro Culture of Embryos

The embryos are postactivated and cultured in vitro: the activated embryos incubated in TCM199 washing medium containing FBS or BSA are postactivated by incubating in cycloheximide solution or DAMP(4-dimethylaminopurine) solution, and cultured in vitro under an environment of 5% $CO_2$, or a mixture of 5% $CO_2$, 7% $O_2$ and 88% $N_2$. The said cycloheximide solution or DAMP solution is prepared by adding cycloheximide dissolved in ethanol or DAMP to media for in vitro culture, respectively. The media for in vitro culture include mTALP(see: Table 1), mSOF(see: Table 2) and mCR2aa(see: Table 3) medium, all of which comprise NaCl, KCl, $NaHCO_3$, $NaH_2PO_4$, $CaCl_2$, Na-lactate, glucose, phenol red, BSA, kanamycin, essential amino acids, non-essential amino acids and L-glutamine.

Optionally, the embryos cultured in vitro are stored by freezing for later use, and subjected to thawing when they are intended to be used. To freeze the embryos, they are washed with PBS containing FBS, put in a freezing medium containing penicillin-streptomycin, $CaCl_2$, glucose, $MgCl_2$, Na-pyruvate and PBS. Then, the embryos in the freezing medium are subjected to slow freezing, followed by rapid freezing in liquid $N_2$. When the frozen embryos are taken from liquid $N_2$ and thawed, they are put in the air for about 5 seconds and then thawed in warm water. To remove the freezing medium from the thawed embryos, they are put serially in media containing glycerol from its high concentration to low concentration.

TABLE 1

| mTALP medium | |
|---|---|
| Ingredient | Concentration |
| NaCl | 93.1~103.4 mM |
| KCl | 3.1 mM |
| $NaHCO_3$ | 25 mM |
| $NaH_2PO_4$ | 0.36 mM |
| Na-lactate | 15 mM |
| $CaCl_2 \cdot 2H_2O$ | 1.7 mM |
| $MgCl_2 \cdot 6H_2O$ | 0.5 mM |
| Na-pyruvate | 0.45 mM |
| Glucose | 1.5 mM |
| Phenol red | 10 $\mu g/l$ |
| BSA | 8 mg/ml |
| Kanamycin | 0.75 $\mu g/ml$ |
| EAA (essential amino acids) | 2% |
| NEAA (non-essential amino acids) | 1% |
| L-glutamine | 1 mM |
| ITS (insulin-transferrin-sodium selenite media supplement) | 0.5% |

TABLE 2 mSOF medium

| Ingredient | Concentration |
|---|---|
| NaCl | 99.1~106 mM |
| KCl | 7.2 mM |
| NaHCO$_2$ | 25 mM |
| NaH$_2$PO$_4$ | 1.2 mM |
| Na-lactate | 5 mM |
| CaCl$_2$·2H$_2$O | 1.7 mM |
| MgCl$_2$·6H$_2$O | 0.5 mM |
| Na-pyruvate | 0.3 mM |
| Glucose | 1.5 mM |
| Phenol red | 10 μg/l |
| BSA | 8 mg/ml |
| Kanamycin | 0.75 μg/ml |
| EAA (essential amino acids) | 2% |
| NEAA (non-essential amino acids) | 1% |
| L-glutamine | 1 mM |
| ITS | 0.5% |

TABLE 3 mCR2aa medium

| Ingredient | 1$^{st}$ Culture Medium (1–4 days) | 2$^{nd}$ Culture Medium (After 4$^{th}$ day) | Washing Medium |
|---|---|---|---|
| NaCl | 114 mM | 114 mM | 114 mM |
| KCl | 3.1 mM | 3.1 mM | 3.1 mM |
| NaHCO$_3$ | 25 mM | 25 mM | 2 mM |
| NaH$_2$PO$_4$ | 0.35 mM | 0.35 mM | 0.34 mM |
| Na-lactate | 15 mM | 15 mM | 15 mM |
| CaCl$_2$·2H$_2$O | 2 mM | — | 2 mM |
| MgCl$_2$·6H$_2$O | 0.5 mM | 0.5 mM | 0.5 mM |
| EAA | — | 1% | — |
| NEAA | 1% | 1% | 1% |
| Insulin | 1% | 1% | 1% |
| Glatamine | — | 1 mM | 1 mM |
| Glycine | 0.37 mM | 0.37 mM | 0.37 mM |
| Citric Acid | 0.33 mM | 0.33 mM | 0.33 mM |
| HEPES | — | — | 10.5 mM |
| Na-pyruvate | 0.3 mM | 0.3 mM | — |
| Glucose | — | 1.5 mM | — |
| Phenol red | 10 μg/l | 10 μg/l | 10 μg/l |
| BSA | 3 mg/ml | — | 3/ml |
| FBS | — | 10% | — |
| Kanamycin | 0.75 μg/ml | 0.75 μg/ml | 0.75 μg/ml |

Step 6: Production of Cloned Cows

The embryos cultured in vitro are transferred into surrogate cows: the embryos in PBS containing FBS are implanted to uterus of surrogate cows. Based on the method described above, the present inventors produced embryos, *Bos taurus coreanae* embryos/TcEar and SNU2(Bovine NT embryo), by using ear cells of Korean cow(*Bos taurus coreanae*) and Holstein as nucleus donors, respectively. These two embryos were deposited with an international depositary authority, KCTC(Korean Collection for Type Cultures; KRIBB #52, Oun-dong, Yusong-ku, Taejon, 305–333, Republic of Korea) on Dec. 31, 1999 and Mar. 10, 2000, under the accession numbers of KCTC 0719BP and KCTC 0753BP, respectively. The present inventors obtained normal cloned offspring by transferring these embryos into surrogate cows.

The present invention is further illustrated in the following examples, which should not be taken to limit the scope of the invention.

EXAMPLE 1

Preparation of Donor Cells and Recipient Oocytes

To prepare donor cells, tissue lined with the inner side of ear skin was collected from Korean cows(*Bos taurus coreanae*), washed with PBS(phosphate buffered saline, Gibco BRL, Life Technologies, USA), and minced into 100 mesh size. Then, the tissue was incubated in PBS containing 0.25% trypsin, 1 mM EDTA and 1 mg/ml collagenase type II for 1 hr under an environment of 39° C., 5% $CO_2$. After the tissue was digested with the enzymes, it was centrifuged at 1,500 rpm for 2 minutes, and suspended in DMEM (Dulbecco's modified Eagle's medium, Gibco BRL, Life Technologies, USA) supplemented with 10% FBS, 1% NEAA(non-essential amino acids) and 1% penicillin-streptomycin. The suspension was transferred to dishes for cell culture and incubated under an environment of 39° C., 5% $CO_2$ to give a somatic cell line. After that, the cells were trypsinized in solution containing 0.25% trypsin and 1 mM EDTA, and the cell number was adjusted to be $2\times10^4$ cells/ml to aliquot the cells in effendorf-tubes.

FIG. 1 depicts the somatic cells isolated as single cells for nucleus donor.

On the other hand, for recipient oocytes, follicles of which size was about 2 to 6 mm in diameter were aspirated from ovaries of Korean cows with a 10 ml syringe having an 18 G needle. Then, the follicular fluid were transferred into a 100 mm dish with a grid(the length between lines was 1 cm) drawn on its bottom, and oocytes with homogeneous cytoplasm and sufficient number of cumulus cell layers around them were screened. The selected oocytes were washed three times with 2 ml of TCM199 washing medium(see: Table 4) in 35 mm dishes, and subsequently, once with TCM199 culture medium(see: Table 5). Finally, the oocytes were cultured in TCM199 culture medium containing 0.1% estradiol solution(see: Table 6), 2.5% follicle stimulating hormone solution(see: Table 7) and 10% FBS to give recipient oocytes.

TABLE 4

TCM199 washing medium

| Ingredient | Concentration |
|---|---|
| TCM powder | Gibco 31100-027 |
| HEPES | 10 mM |
| NaHCO$_3$ | 2 mN |
| BSA | 0.5% W/V |
| Penicillin-streptomycin | 1% (penicillin 10000 U/ml, streptomycin 10 mg/ml) |

TABLE 5

TCM199 culture medium

| Ingredient | Concentration |
|---|---|
| TCM liquid | Gibco 11150-059 |
| Na-pyruvate | 1 mM |
| Penicillin-streptomycin | 1% (penicillin 10000 U/ml, streptomycin 10 mg/ml) |

TABLE 6

Estradiol solution

| Ingredient | Concentration |
|---|---|
| Estradiol | 5 mg |
| Ethanol | 10 ml |

TABLE 7

Follicle stimulating hormone solution

| Ingredient | Concentration |
| --- | --- |
| Follicle stimulating hormone | 2 AU |
| TCM199 culture medium | 10 ml |

EXAMPLE 2

Nuclear Transfer of Somatic Cells

Figure 2:
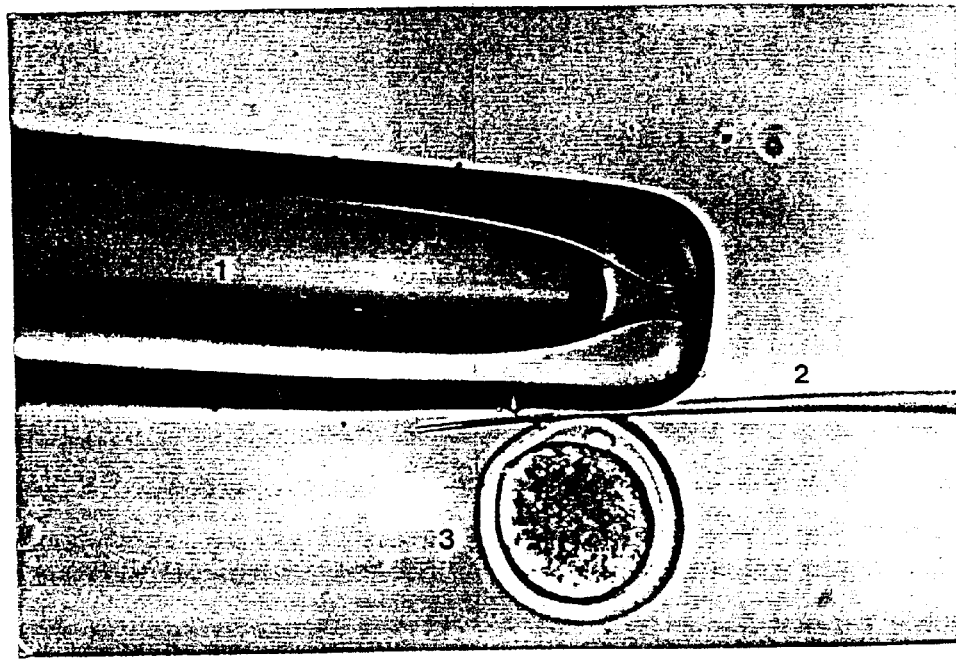
FIG. 2 is a photograph showing the process of cutting zona pellucida of a recipient oocyte with a holding pipette and cutting pipette.
Figure 3:
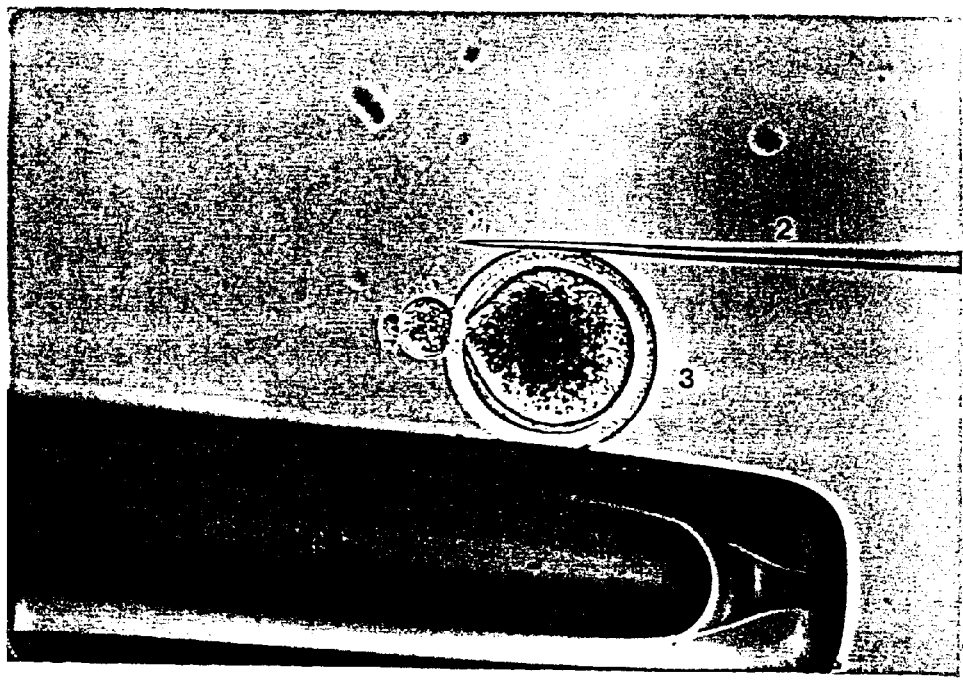
FIG. 3 is a photograph showing the process of enucleation by removing the first polar body and nucleus from a recipient oocyte.

The recipient oocytes prepared in Example 1 were washed once with TCM199 washing medium and transferred in 0.1% hyaluronidase(Sigma Chemical Co., U.S.A.) solution prepared by mixing 1 ml of TCM199 washing medium with 111 μl of hyaluronidase stock solution(10 mg/ml in TCM199 washing medium). After cumulus cells were removed from the oocytes in the presence of 0.1% hyaluronidase, the denuded oocytes were washed three times and incubated in TCM199 washing medium. Then, the oocytes were transferred to cytochalasin B(Sigma Chemical Co., U.S.A.) solution prepared by mixing 1 ml of TCM199 washing medium containing 10% FBS with 1 μl of cytochalasin stock solution (7.5 mg/ml in DMSO), and zona pellucida of each oocyte was cut by employing micromanipulator to make a slit through which 10 to 15% of cytoplasm can be squeezed out of the oocyte to give an enucleated oocyte. The enucleation step is more specifically illustrated as following: a working dish was put on the micromanipulator plate, and the micromanipulator was equipped with a holding pipette on its left arm and a cutting pipette on its right arm. Then, the holding pipette and cutting pipette were placed in the direction of 9 o'clock and 3 o'clock, respectively, and adjusted to move freely in all directions by placing a pipette controller in the middle. These two pipettes were further adjusted to let them not touch the working dish and their tips placed to the middle of a microdroplet by moving them up and down over the microdroplet. Then, the oocytes were transferred from TCM199 washing medium to cytochalasin B solution by employing washing mouth pipettes(>200 μm inner diameter). The micromanipulator was first focused on the oocyte by using its coarse adjustment knob and fine adjustment knob, and the focus was further adjusted by moving the two pipettes up and down. The oocyte was placed with its first polar body oriented toward the direction of 12 o'clock, and the holding pipette was placed close to the oocyte in the direction of 9 o'clock of the oocyte to fix the oocyte by applying hydraulic pressure. FIG. 2 shows the process of cutting zona pellucida of the oocyte with the holding pipette and cutting pipette. As shown in FIG. 2, the oocyte was penetrated by the cutting pipette(2) from the direction of 1 o'clock to the direction of 11 o'clock with special care not to damage the cytoplasm of the oocyte. After that, hydraulic pressure was applied to the holding pipette(1) to separate the oocyte(3), and the holding pipette was contacted with the cutting pipette penetrating the zona pellucida bordering on the upper part of the first polar body to cut the portion of zona pellucida by rubbing the two pipettes. The slit on the oocyte made above was used for both enucleation and donor cell injection. FIG. 3 depicts the process of enucleation removing the first polar body and nucleus from the oocyte. As shown in FIG. 3, the oocyte(3) was placed with its slit oriented vertically, held with the holding pipette(1) on its lower part to prevent it from moving, and squeezed mildly on its upper part with the cutting pipette(2) to give an enucleated oocyte. The enucleated oocyte was washed three times with TCM199 washing medium and incubated in TCM199 culture medium.

After that, donor cells prepared in advance were transferred to enucleated oocytes by employing micromanipulator. First, 4 μl of injection microdroplet was made on the middle of the working dish by using PHA-P solution prepared by mixing 400 μl of TCM199 washing solution and 100 μl of PHA-P(phytohemagglutinin) stock solution(0.5 mg/ml in TCM199 washing solution). And then, two microdroplets for donor cells were made with one above and the other below the injection microdroplet on the same working dish by using PBS containing 1% FBS. After these microdroplets were spread over with mineral oil, the working dish was placed on the micromaniulator plate.

Figure 4:
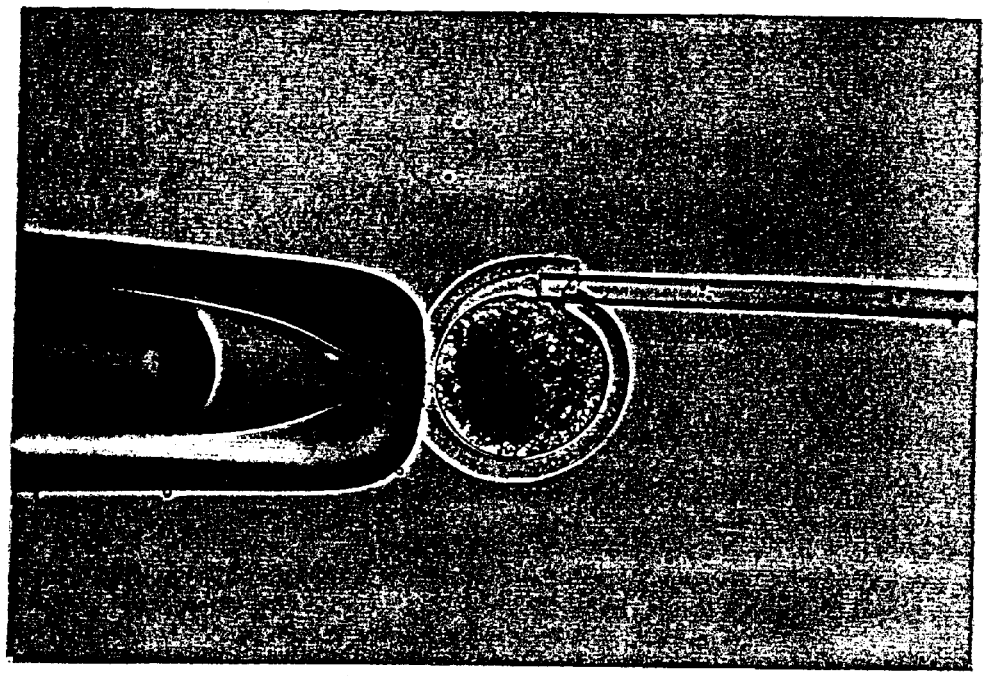
FIG. 4 is a photograph showing the process of transferring a somatic cell into an enucleated oocyte with a holding pipette and injection pipette.

The cutting pipette installed on the micromanipulator was substituted with an injection pipette. The enucleated oocytes were washed three times with TCM199 washing medium and transferred into the injection microdroplet. The donor cells were drawn up into the injection pipette and transferred into the injection microdroplet. FIG. 4 shows the process of transferring a somatic cell into an enucleated oocyte. As shown in FIG. 4, the enucleated oocyte was placed with its slit oriented toward the direction of 1 o'clock, fixed by using the holding pipette, and injected with the donor cell through the slit by employing the injection pipette and hydraulic pressure to give a reconstructed embryo. The embryo was washed three times with and incubated in TCM199 washing medium.

EXAMPLE 3

Electrofusion and Activation

The reconstructed embryos were subjected to electrofusion employing an Electro Cell Manipulator(ECM 2001, BTX, USA), followed by activation. 15 μl of mannitol solution containing 0.28 M mannitol, 0.5 mM HEPES(pH 7.2), 0.1 mM MgSO$_4$ and 0.05% BSA was added to TCM199 culture medium containing the reconstructed embryos by employing a mouth pipette for washing. After 1 minute's incubation in the said medium, the embryos were incubated for 1 minute in mannltol solution supplemented with TCM199 washing solution, and finally transferred into mannitol solution by employing the mouth pipette for washing. The chamber(3.2 mm chamber No. 453) of the Electro Cell Manipulator was filled with mannitol solution supplemented with TCM199 washing medium, and then the embryos were placed in the chamber with their donor cell part facing the cathode. After the embryos were electrofused by applying DC pulse of 0.75 to 2.00 kV/cm twice with one second's interval for 15 μs each time, they were transferred into and washed three times with TCM199 washing medium by way of mannitol solution.

To activate the electrofused embryos, they were incubated in the dark for 4 minutes in ionomycin(Sigma Chemical Co., USA) solution which was TCM199 washing medium containing 5 μM ionomycin and 1% BSA. The ionomycin stock solution was prepared by dissolving 1 mg of ionomycin in 1.34 ml of DMSO. The activated embryos were incubated for 5 minutes in a 35 mm dish containing TCM199 washing medium supplemented with 10% FBS to remove ionomycin from the embryos.

EXAMPLE 4

Postactivation and in vitro Culture of the Electrofused Embryos

The activated embryos were postactivated for 4 hrs in 25 μl of cycloheximide(Sigma Chemical Co., USA) solution prepared by adding cycloheximide stock solution(10 mg/ml in ethanol) to an in vitro culture medium, mTALP in a final concentration of 10 μg/ml. Then, the embryos were screened, and the selected embryos were incubated for 7 days under an environment of 39° C., 5% $CO_2$.

By employing the method described in Examples 1 to 4, the present inventors produced an embryo, Bos taurus coreanae by using ear cells of Korean cow(Bos taurus coreanae) as a nucleus donor, and deposited the embryo with an international depositary authority, KCTC(Korean Collection for Type Cultures; KRIBB #52, Oun-dong, Yusong-ku, Taejon, 305–333, Republic of Korea) on Dec. 31, 1999 under an accession number of KCTC 0719BP.

EXAMPLE 5

Production of Embryos Employing Ear Cells of Holstein

The present inventors produced another embryo, SNU2 (Bovine NT embryo) by employing the same method described in Examples 1 through 4 except using ear cells and oocytes of Holstein as nuclear donor and recipient oocyte, respectively. The embryo was deposited with an international depositary authority, KCTC(Korean Collection for Type Cultures; KRIBB #52, Oun-dong, Yusong-ku, Taejon, 305–333, Republic of Korea) on Mar. 10, 2000 under an accession number of KCTC 0753BP.

EXAMPLE 6

Freeze and Thaw of Embryos and Implantation

The embryos were frozen for long-term storage. First, a freezing medium(see: Tables 8 and 9) was distributed into 35 mm dishes, and a freezer was turned on to be maintained at −5° C. The embryos selected for freezing were washed with PBS containing 10% FBS, and incubated in the freezing medium for 20 minutes. Then, the embryos were drawn up into a 0.25 ml French straw to let the straw have the freezing medium containing the embryos in the middle and two layers of air at both ends. After the straw was heat-sealed at both ends by using a heated forcep, it was placed into the freezer, held at −5° C. for 5 minutes, and seeded with a forcep prechilled by liquid $N_2$. After seeding, the straw was cooled down at a rate of −0.3° C./min to −30° C., held for 10 minutes when the temperature reached −30° C. Finally, the embryos were stored in a liquid $N_2$ tank.

TABLE 8

Freezing PBS

| Ingredient | Concentration |
| --- | --- |
| PBS (1x) | Gibco 14190-144 |
| Na-pyruvate | 0.033 mM |
| Glucose | 0.15 mM |
| $CaCl_2·2H_2O$ | 0.171 mM |
| Penicillin-streptomycin | 1% (penicillin 10000 U/ml, streptomycin 10 mg/ml) |
| $MgCl_2·6H_2O$ | 0.049 mM |

TABLE 9

Freezing medium

| Ingredient | Concentration |
| --- | --- |
| Freezing PBS (Table 8) | 2.25 ml (45%) |
| Fetal bovine serum (FBS) | 2.25 ml (45%) |
| Glycerol | 0.5 ml (10%) |

To thaw the frozen embryos, a thawing medium containing PBS supplemented with 20% FBS was prepared in 35 mm dishes, and added with glycerol to give thawing media each having 0%, 3% and 6% glycerol(see: Tables 8 and 10). Then, the frozen straw was taken out from the liquid $N_2$, held in the air for 5 seconds, and thawed in a container (>20cm in diameter) containing warm water(30° C.). After thawing, the straw was cut on the air layers at both ends, and the medium containing the embryos was collected. The embryos were examined under the microscope. To remove the freezing medium from the embryos, they were consecutively incubated in the thawing media containing 6% glycerol, 3% glycerol and 0% glycerol, each for 5 minutes.

TABLE 10

Thawing media

| Ingredient | 6% Glycerol PBS | 3% Glycerol PBS | 0% Glycerol PBS |
| --- | --- | --- | --- |
| PBS | (Table 8) | (Table 8) | (Table 8) |
| BSA | 0.5% | 0.5% | 0.5% |
| Glycerol | 5% | 3% | 0% |
| Sucrose | 0.3 M | 0.3 M | 0.3 M |

The thawed embryo was placed in PBS containing 20% FBS, and drawn up into a 0.25 ml straw. And then, it was transferred into the uterus of a surrogate cow.

EXAMPLE 7

Comparison of Embryos Employing Various Nucleus Donors

To compare the differences among the embryos produced by employing different nucleus donors, Bos taurus coreanae embryos/TcEar(KCTC 0719BP) and SNU2(KCTC 0753BP) produced in Example 4 and Example 5, respectively, were implanted to surrogate cows, and compared regarding the following terms: number of electrofused oocytes, electrofusion rate(%), division rate(%), number(%) of morulae/blastocysts developed, number of transferred embryos and number(%) of offsprings(see: Table 11). Number(%) of morulae/blastocysts represents the ratio of embryos developed by in vitro culture to the stage right before implantation over the total embryos produced by nuclear transfer.

TABLE 11

Comparison of embryos

|  | No. of electrofused oocytes | Electrofusion rate (%) | Division rate (%) | No. (%) of morulae/ blastocysts | No. of transferred embryos | Delivery rate (%) |
|---|---|---|---|---|---|---|
| Holstein | 1784 | 79.0 | 92.6 | 44.9 | 177 | 48.0 |
| Korean cow | 1523 | 83.1 | 86.8 | 47.8 | 196 | 57.1 |

As shown in Table 11, there was no significant difference between ear cells of Korean cow and Holstein for nucleus donors when the two cases were compared in terms of production and culture of embryos. This result indicates that the method for producing cloned cows of the present invention can be applied to other cow species without any specificity. In addition to broad application for nucleus donors, the method of the present invention can significantly improve the yield of the reconstructed embryos, since the number(%) of morulae/blastocysts and delivery rate of the present invention are much higher than those of prior arts(see: Goto et al., Anim. Sci. Journal, 70:243–245, 1999; Zakhartchenko et al., J. Reprod. Fertil., 115:325–331, 1999; Hill et al., Biol. Reprod., 62:1135–1140, 2000; Kubota et al., Proc. Natl. Acad. Sci., USA, 94:990–995, 2000).

EXAMPLE 8

Production of Embryos by Employing Uterine Cells of Korean Cow as Nucleus Donor

An embryo was produced by employing the same procedure described in Examples 1 through 4 except that the donor cells were isolated from the uterus of Korean cow.

EXAMPLE 9

Comparison of Embryos Employing Various Donor Tissues

To compare the differences among the embryos produced by employing the different donor tissues, the embryos produced in Examples 4 and 8, respectively, were implanted to surrogate cows as described in Example 6, and examined in the same way as Example 7(see: Table 12)

TABLE 12

Developmental rate of embryos depending on the source of nucleus donors

|  | No. of electrofused oocytes | Electrofusion rate (%) | Division rate (%) | No. (%) of morulae/ blastocysts | No. of transferred embryos | Delivery rate (%) |
|---|---|---|---|---|---|---|
| Uterus | 1325 | 74.3 | 91.2 | 43.1 | 182 | 48.4 |
| Ear | 1523 | 83.1 | 86.8 | 47.8 | 196 | 57.1 |

As shown in Table 12, there was no significant difference between different tissues for donor cells when the two cases were compared in terms of production and culture of embryos. This result shows that the method for producing cloned cows of the present invention can be applied to many cell types, rather than specific somatic cells.

As clearly illustrated and explained above, the present invention provides a method for producing cloned cows comprising steps of maturing oocytes in vitro, preparing donor somatic cells and enucleated oocytes, nuclear transfer, electrofusion and subsequent activation, postactivation and in vitro culture, and, transfer of embryos into surrogate cows. In accordance with the method for producing cloned cows of the invention, somatic cell-derived cloned cows can be produced in an efficient manner by employing reconstructed embryos obtained through highly improved nuclear transfer technique, which makes possible mass production of pharmaceuticals and organs in medical and livestock industry and facilitates its universal application in many other related fields.

Various modifications of the invention in addition to those shown and described herein will be apparent to those skilled in the art from the foregoing descriptions. Such modifications are also intended to fall within the scope of the appended claims.

What is claimed is:
1. A method for producing cloned cows which comprises the step of:
(i) preparing donor somatic cell lines collected from cows;
(ii) maturing oocytes collected from a cow ovary in vitro;
(iii) removing cumulus cells surrounding the oocytes, cutting a portion of the zona pellucida of the matured oocytes to make a slit, and squeezing out a portion of the cytoplasm including the first polar body through the slit to produce enucleated recipient oocytes;
(iv) transferring a nucleus to the recipient oocyte by injection of the whole donor cells to the enucleated recipient oocytes through the slit followed by the subsequent electrofusion in a $Ca^{2+}$ free medium and activation of the electrofused cells in ionomycin solution in the dark to produce embryos;
(v) post-activating and culturing the embryos in a medium mTALP, mSOF or mCR2aa; and
(vi) transferring the culturing embryos into surrogate cows to undergo full fetal development and parturition, whereby cloned calves are generated.
2. The method for producing cloned cows of claim 1, wherein the somatic cell lines prepared in Step(i) include cells collected from uterine flushing fluid, endometrium, oviduct, ear or muscle, cumulus cells or fetal fibroblasts.

3. The method for producing cloned cows of claim 1, wherein the somatic cell lines are stored by subculture, serum starvation culture or freezing.

4. The method for producing cloned cows of claim 1, wherein the cumulus cells surrounding the oocytes in Step (iii) are physically removed with a denuding pipette after treatment of hyaluronidase.

5. The method for producing cloned cows of claim 1, wherein the enucleation of oocytes in Step(iii) is carried out by making a slit on the oocyte by cutting it with micromanipulator; placing the oocyte with its slit oriented vertically and holding a lower part of the oocyte with a holding pipette to prevent the cell from moving; squeezing the upper part of the oocyte with a cutting pipette to let 10 to 15% of cytoplasm containing the first polar body out of the oocyte through the slit.

6. The method for producing cloned cows of claim 1, wherein the electrofusion in Step(iv) is carried out by applying DC pulse of 0.75 to 2.00 kV/cm twice with one second intervals.

7. The method for producing cloned cows of claim 1, wherein the postactivation in Step(v) is carried out by culturing embryos in cycloheximide solution or DMAP(4-dimethylaminopurine) solution.

8. The method for producing cloned cows of claim 1, further comprising a step of storing embryos cultured in vitro in Step(v) for later use after freezing the embryos in a freezing medium containing penicillin-streptomycin, $CaCl_2$, glucose, $MgCl_2$, Na-pyruvate and phosphate buffered saline.

* * * * *